United States Patent [19]

Leach

[11] Patent Number: 5,320,617
[45] Date of Patent: Jun. 14, 1994

[54] METHOD OF LASER-ASSISTED PROSTATECTOMY AND APPARATUS FOR CARRYING OUT THE METHOD

[76] Inventor: Gary E. Leach, 2630 Winrow Ct., Rowland Heights, Calif. 91748

[21] Appl. No.: 81,234

[22] Filed: Jun. 25, 1993

[51] Int. Cl.$^5$ .............................................. A61B 17/36
[52] U.S. Cl. ...................................... 606/15; 604/21; 128/898; 607/89
[58] Field of Search ............................. 606/7, 13–15; 607/88, 89; 604/20–22, 43; 128/898, 4, 6

[56] References Cited

U.S. PATENT DOCUMENTS

| | | | |
|---|---|---|---|
| 4,445,892 | 5/1984 | Hussein et al. | 606/15 |
| 5,048,508 | 9/1991 | Storz et al. | 128/4 |
| 5,053,033 | 10/1991 | Clarke | 606/15 |
| 5,083,549 | 1/1992 | Cho et al. | 604/21 |
| 5,207,672 | 5/1993 | Roth et al. | 606/7 |
| 5,217,454 | 6/1993 | Khoury | 606/14 |

*Primary Examiner*—Stephen C. Pellegrino
*Assistant Examiner*—M. Peffley

[57] ABSTRACT

A method of laser-assisted prostatectomy which is based on the use of special laseroscope with continuous flow of the flushing and cooling liquid is provided. The method consists of inserting the above laseroscope into the patient's urethra with the laser fiber tip positioned at the prostate gland area, inserting a balloon catheter through the laseroscope to the urinary bladder neck, inflating the balloon of the catheter, initiating an inflow of washing and cooling liquid to the operating area, which is isolated from the urinary bladder by the balloon catheter, inserting a laser fiber into the laseroscope, firing the laser fiber and directing a laser beam laterally from the laser fiber onto the prostatic gland for directing the laser beam to the required area. The method is carried out by means of an apparatus comprising a tubular sheath (10) with three guide tubes, i.e., a guide tube (13) for an optical lens system (12), a second guide tube (14) for a laser fiber (16), and a third or auxiliary guide tube (18) for interchangeably inserting: a cleaning brush (19), which may rotate and reciprocate in the guide tube (18) for cleaning the operating tip of the laser fiber (16); an ultrasonic probe (40) for measuring the degree and depth of ablation of the prostatic tissue; and a balloon catheter (42) for the occlusion of the bladder neck. Spaces (15a) and (15b) between the inner surface of the sheath (10) and the outer surfaces of the guide tubes form mutually isolated channels for the continuous supply and removal of the flushing and cooling liquid.

15 Claims, 5 Drawing Sheets

METHOD OF LASER-ASSISTED PROSTATECTOMY AND APPARATUS FOR CARRYING OUT THE METHOD

BACKGROUND OF THE INVENTION

1. Field of the Invention

The present invention relates to urology, in particular, to a method and apparatus for treating patients with benign prostatic hyperplasia.

2. Description of Prior Art Technique

At the present time, laser technologies find wide application in medicine for surgery. In particular, in the field of urology, a conventional cystoscope is commonly used to perform laser operations in the urethra, bladder, and prostate (see Urology Johnson, D. E., Laser Prostatectomy Using Right-Angle Delivery System. Lasers in Urology. Laparascopy and General Surgery, Vol. 1421, p. 36, 1991). A laser fiber is inserted into the axial channel of the cystoscope, while a liquid which is used for filling the urinary bladder is supplied through the sheath.

In the course of such an operation, for example, a laser prostatectomy, the filling and irrigation liquid is periodically removed from the system. For this purpose, the operation is discontinued, a valve is opened, all or a part of the existing liquid is drained from the bladder and replaced with fresh liquid. The operation is then resumed. Poor heat-removal conditions which arise in the operation area during operation with the use of the above-described conventional cystoscope sometimes lead to the overheating of the metal laser tip to such an extent that it has to be replaced before the operation may proceed.

Very often during the operation the laser tip comes into contact with tissue in the prostate affected area. This causes the prostate tissue to adhere to the reflecting surface of the laser-beam emitting device. As a result, the operation has to be discontinued, and the laser fiber has to be removed for cleaning purposes. This is an extremely inconvenient and time-consuming operation.

Furthermore, the radially inwardly directed forces developed by the enlarged prostate constrict the prostatic part of the urethra, whereby the field of vision is obscured.

OBJECTS OF THE INVENTION

It is an object of the present invention to provide a method and an apparatus for laser-assisted prostatectomy which ensure improved cooling conditions in the operation area, prolong the service life of the apparatus, and make it possible to carry out the operation continuously without being forced to interrupt it to clean the working area of the laser fiber. Another object is to provide an apparatus which is extremely convenient and universal in use, simple in construction, and improves conditions for the observation of the operation site. A further object is to provide means for the periodical cleaning of the laser-emitting orifice.

Other objects and advantage of the invention will be understood after the consideration of the ensuing description with the accompanying drawings.

SUMMARY OF THE INVENTION

The invention provides an endoscopic laser instrument for transurethral operations which comprises an elongated tubular sheath containing three longitudinally arranged guide tubes. The first tube is for guiding an axially moveable laser fiber that has at its distal end lateral laser-beam emitting openings and that can be turned around its longitudinal axis. The first tube is slidingly installed in a sleeve so that the distal tip of the tube can be moved back and forth. This makes it possible to position a distal tip of the tube closer to a distal end of the laser fiber and thus to concentrate the washing and cooling liquid in the operating area.

The second guide tube is for guiding a fiber-optic lens system used to observe the operation site. The third auxiliary guide tube is for guiding an auxiliary instrument such as: an ultrasonic sound for determining the depth of ablation of the tissue by a laser beam; a balloon catheter for closing the bladder neck opening and thus for isolation of the prostatic part of the urethra from the urinary bladder; or a cleaning brush which can be moved axially within the above-mentioned third guide tube and rotated from a drive motor connected to the proximal end of the brush. The space between the inner surface of the tubular sheath and the outer surface of all three inner guide tubes forms at least two isolated channels, each such channel being connected at its proximal end through a shut-off valve either to a source of the supply of a flushing and cooling liquid, or to a reservoir for the removal of the waste liquid. The laser-fiber guide tube is also connected at its proximal end through a shut-off valve to the source of the supply of the flushing and cooling liquid.

With the use of the above instrument, the method is carried out in the following manner.

After preliminary cystoscopy is completed, the above-described sheath is inserted into the patient's urethra to the operating area. The laser fiber and the balloon catheter are then inserted into their respective guide tubes. The balloon is then inflated within the bladder to a diameter exceeding the inner diameter of the bladder neck. As a result, the balloon catheter isolates the area between the inflated balloon and the tip of the instrument's sheath. The cooling and flushing liquid is then caused to circulate through the restricted small-volume area between the balloon and the instrument's tip without penetrating to the bladder, which may remain empty. The liquid is continuously fed through the first guide tube for the laser fiber. This liquid cools and flushes the operation area and flows out of the system through isolated axial spaces between the inner surface of the sheath and the outer surfaces of the guide tubes. Alternatively, the liquid may be additionally fed through one of the above-mentioned inner channels and removed through another channel. When it is necessary to check the depth of the ablation of the tissue, the operation can be discontinued, the laser fiber is withdrawn into the sheath and the balloon catheter is replaced by an ultrasonic sound which is connected with a measuring instrument. After determining the degree of penetration into the tissue, the ultrasonic sound is removed, the laser fiber is shifted forward to its operating position, the balloon catheter is reinserted, reinflated, and the operation is resumed.

If it is necessary to clean the laser-emitting openings for removing the adherent prostate tissue, the balloon catheter is deflated and removed from the instrument, while a cleaning brush, which is connected to the rotary drive motor is inserted axially through the auxiliary guide tube to the position of the laser fiber tip. While the brush rotates from the drive motor, it can be moved axially back and forth until the openings are cleaned.

The brush is then removed, the balloon catheter is reinserted, inflated, and the operation is resumed. The pressure developed by the inflow of the liquid expands the prostatic urethra which improves conditions for the observation and cooling of the laser fiber.

DESCRIPTION OF THE APPARATUS OF THE INVENTION

The proposed continuous-flow laseroscope (CFLS) is a specially-designed endoscopic instrument to facilitate the performance of laser-assisted prostate surgery (in particular, laser-assisted transurethral resection of the prostate), as well as assisting in other urological endoscopic procedures requiring the use of a laser fiber (straight firing or angle firing) in the urethra or bladder.

Figure 1:
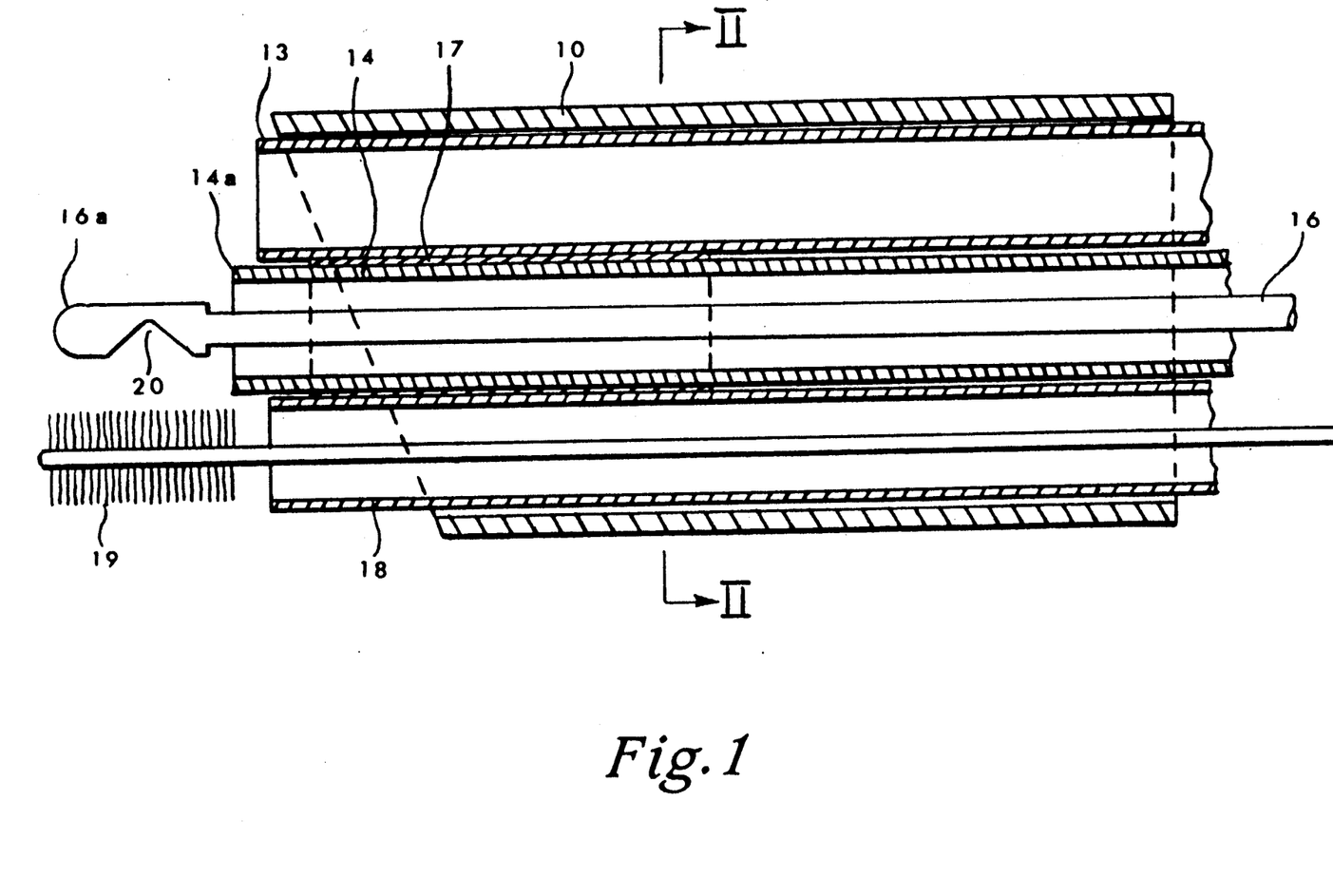
FIG. 1 is a longitudinal sectional view of the distal end of the apparatus of the invention shown on an enlarged scale.
Figure 2:
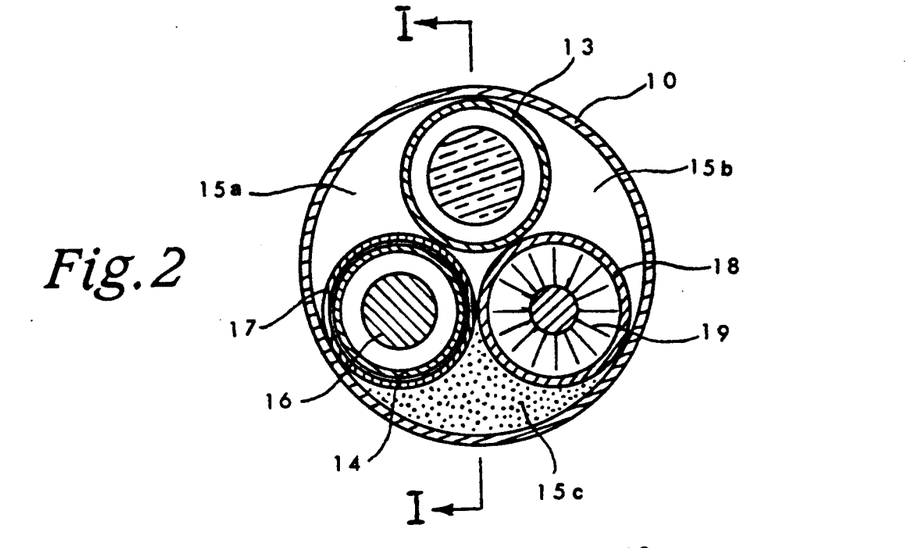
FIG. 2 is a sectional view of the apparatus of FIG. 1 in the direction of line II—II.
Figure 7:
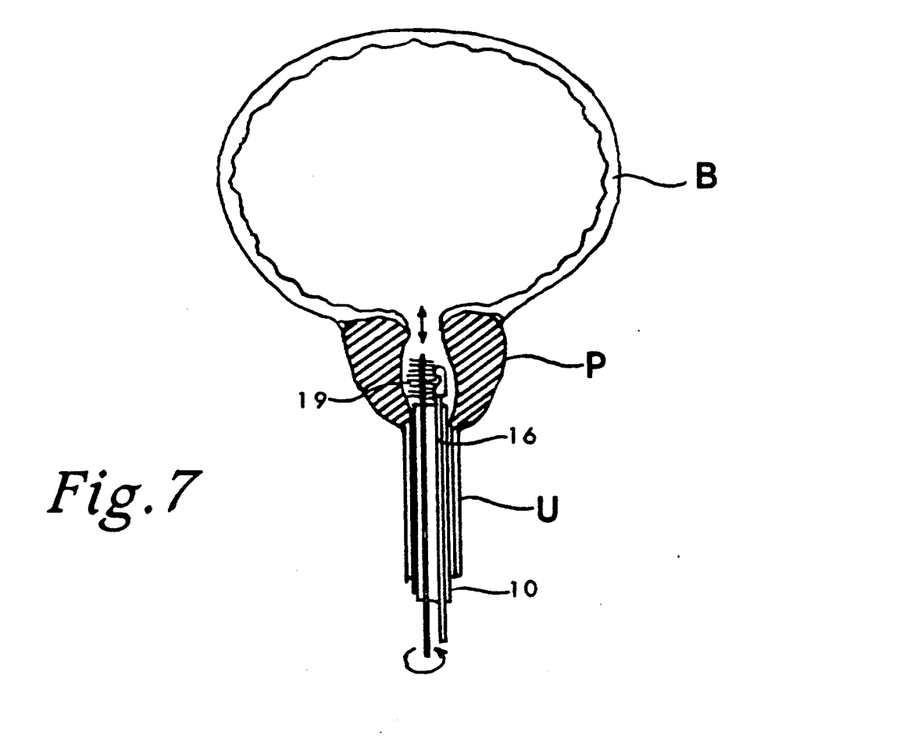
FIG. 7 is a view similar to FIG. 6 illustrating the use of the apparatus without balloon temporary removed and the brush temporary inserted.

FIG. 1 is a longitudinal sectional view of the distal end of the apparatus of the invention shown on an enlarged scale and FIG. 2 is a sectional view along the line II—II of FIG. 1. As shown in FIGS. 1 and 2, the CFLS consists of a tubular outer sheath 10 which contains three tubular channels, i.e., a tubular lens system 12 guided in a tube 13 and designed for the observation of the operation site, a laser-fiber guiding tube 14 which contains the laser fiber 16, and an auxiliary tube 18 which may be used as a guide for a cleaning brush 19, a balloon catheter 42 for the occlusion of the bladder neck and localization of the fluid circulation zone (FIG. 5), or an ultrasonic sound 40 for determining the depth of ablation (FIG. 7). Sound 40 and balloon catheter 42 are standard urological outfits and their use in conjunction with the instrument of the invention will be described in detail later in the section "Operation of the Apparatus".

Laser-fiber guiding tube 14 is slidingly installed in a sleeve 17 so that the distal tip 14a of tube 14 can be moved back and forth. This makes it possible to position a distal tip 14a of tube 14 closer to a distal end 16a of laser fiber 16 and thus to concentrate the washing and cooling liquid in the operating area, when required. Sleeve 17 does not extent over the entire length of guide tube 14 but rather is located at the distal end of the instrument and is rigidly attached to guide tube 13 and auxiliary tube 18.

As shown in FIG. 1, all these tubular elements are arranged in the axial direction of sheath 10. Although, for the sake of convenience of the description all three tubular elements are shown in FIG. 1 one above the other, in reality their position will correspond to that shown in FIG. 2, which is a cross-sectional view along the lines II—II of FIG. 1. Thus, tubes 13, 14, and 18 are tightly fitted into the interior of sheath 10, while a space between the inner walls of sheath 10 and the outer walls of tubes 13, 14, and 18 define channels 15a, 15b which, as will be described later, are used for the return flow of the washing liquid circulating through the system for cooling and washing the operation area. The remaining part 15c of the cavity between the inner walls of sheath 10 and the outer walls of the inner tubes is filled or shaped accordingly, to provide mutual isolation between channels 15a and 15b.

Figure 3:
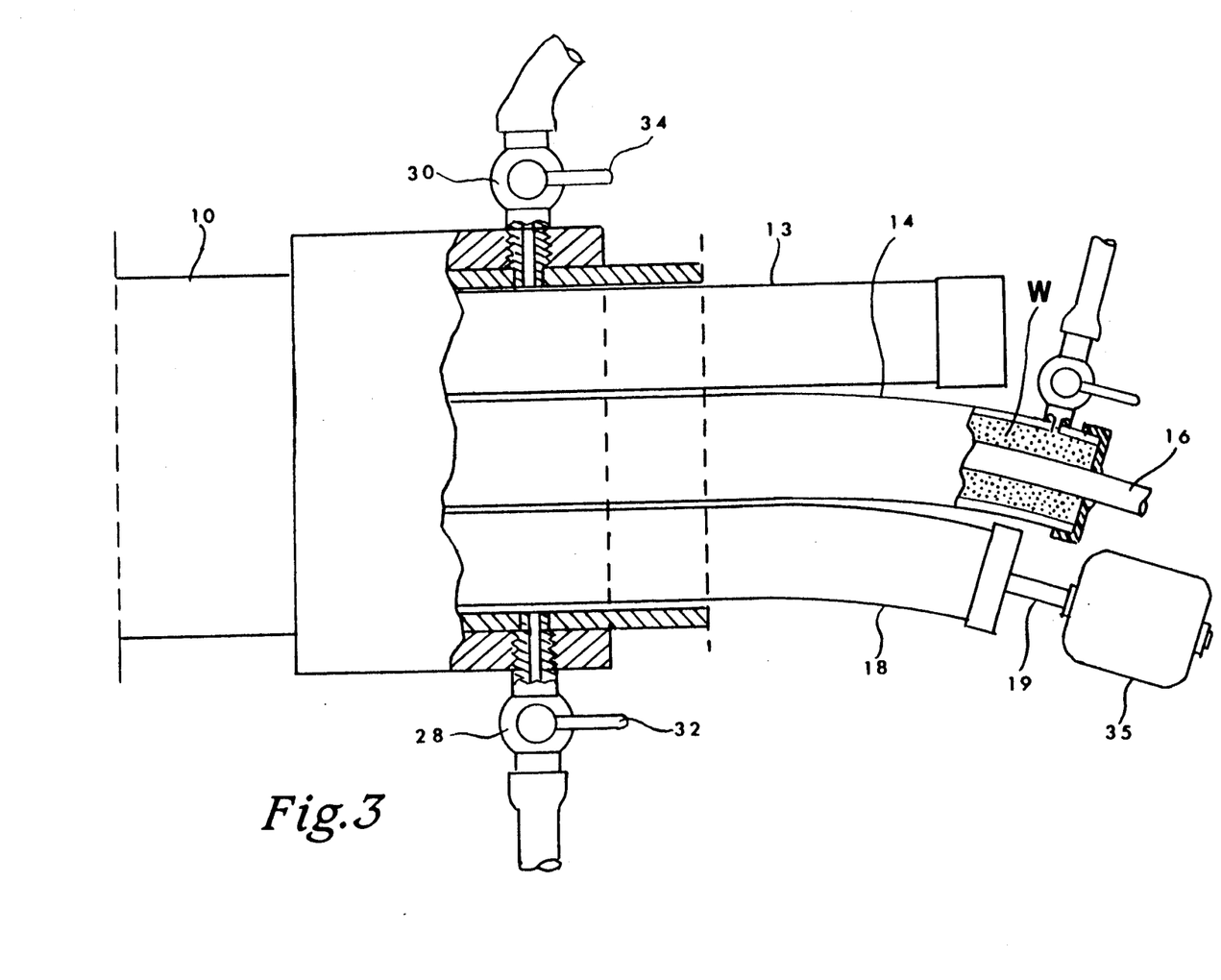
FIG. 3 is a longitudinal sectional view of the proximal end of the apparatus of FIG. 1.

The proximal end of cleaning brush 19 may be connected to a rotating drive such as a hand-held electric motor 35. The housing of motor 35 may be used as a handle for moving cleaning brush 19 along guide channel 18 (FIG. 3). Although in FIG. 1 cleaning brush 19 and laser fiber 16 are shown parallel to each other and at a substantial distance from each other, this is shown only for the convenience of the drawings. In reality, however, sheath 10 will have a diameter, e.g., of 8.33 mm (which corresponds to 25 F) and bristles of brush 19 will be in tight contact with the tip of laser fiber 16.

Laser fiber 16 may slide axially for manipulation during the operation. It is also capable of being turned manually around its longitudinal axis, and has a laser-beam emitting opening 20 for the lateral direction of the laser beams onto the operation site.

In order to prevent the overheating of the laser tip, the instrument is provided with a system for the continuous circulation of liquid. For this purpose, a liquid supply pipe union 24 is branched to the side wall of laser-fiber guiding tube 14 at the proximal end of the instrument. Pipe union 24 is provided with a shut-off valve 26 which may block the supply of liquid into the interior of laser-fiber guiding tube 14.

FIG. 3 is a longitudinal sectional view of the proximal end of the apparatus of FIG. 1. As shown in this drawing, connected to sheath 10 at its proximal end are two pipe unions 28 and 30 with respective shut-off valves 32 and 34. These pipe unions communicate with spaces 15a and 15b and may be used alternatingly for the outflow of the wasted flushing and cooling liquid, or one of them may be used for the inflow (in addition to the inflow through laser-fiber guiding tube 14), while the other is being used for the outflow.

The proximal end of laser fiber 16 is connected to an appropriate laser source such as a diode laser source through a laser-beam delivery system (not shown).

Figure 4:
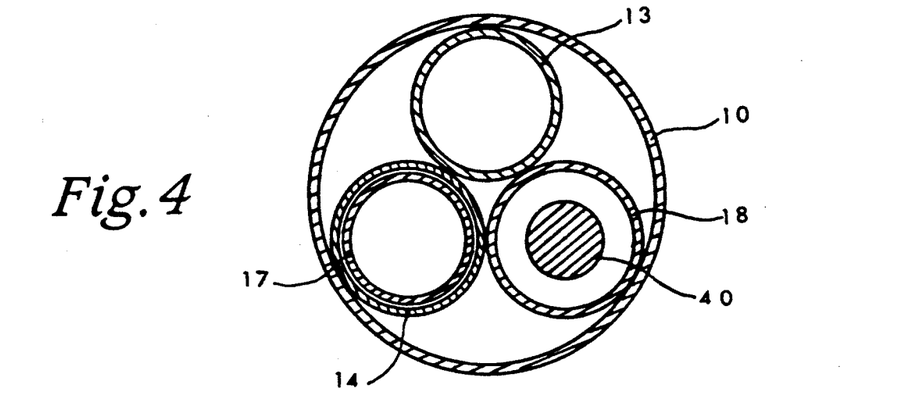
FIG. 4 is the same sectional view as the one shown in FIG. 2 but with an ultrasonic sound inserted into the auxiliary tube instead of cleaning brush.

The proximal end of optical lens system is connected to a conventional optical system for cystoscopy (not shown). The apparatus is also provided with an ultrasonic sound 40 which can be inserted into auxiliary tube 18 instead of cleaning brush 19 for determining the depth of ablation, i.e., the depth of penetration of the laser beam into the prostatic tissue and the thickness of the remaining untreated part of the prostate (FIG. 4).

Figure 5:
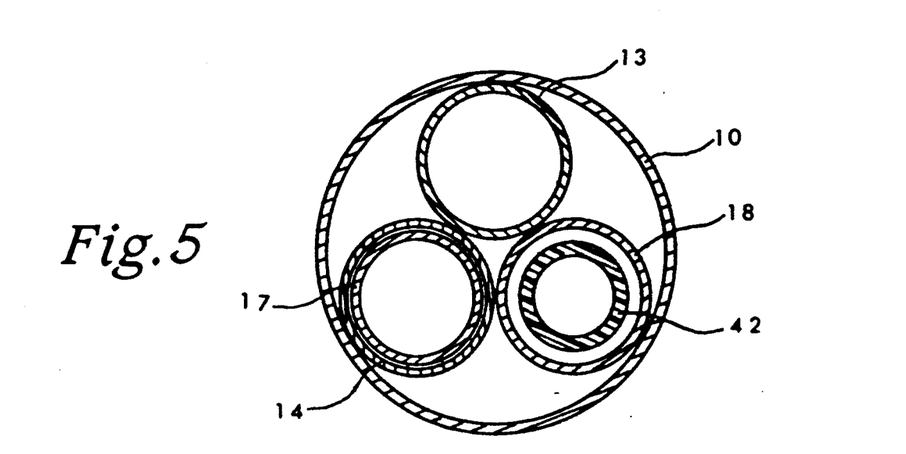
FIG. 5 is the same sectional view as the one shown in FIG. 2 but with a balloon catheter inserted into the auxiliary tube instead of cleaning brush.

Another outfit of the apparatus is a balloon catheter 42 which could be inserted into the same auxiliary tube 18 instead of brush 19 or ultrasound sound 40 (FIG. 5).

The use of brush 19, sound 40, and balloon catheter 42 will be explained in greater detail in conjunction with the description of the operation of the apparatus.

For convenience of insertion into the urinary tract, sheath 10 has an insertable obturator with a flexible tip (not shown) which facilitates the insertion of the sheath and is removed after the apparatus is inserted into a position required for the operation.

Figure 6:
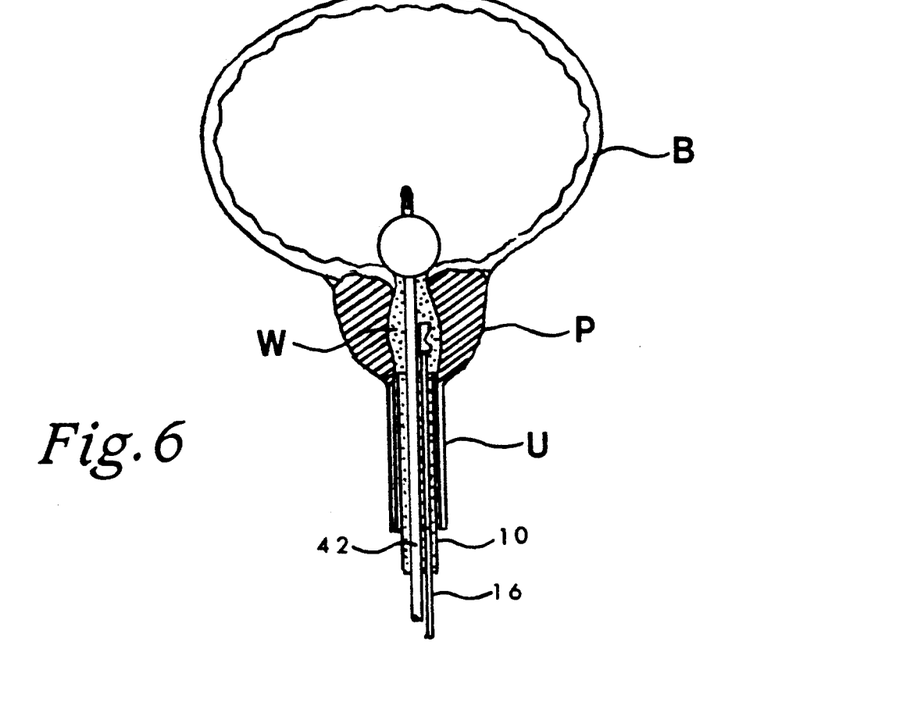
FIG. 6 is a view illustrating the use of the apparatus with a balloon catheter.

Operation of the Apparatus with Balloon Catheter (FIG. 6)

After the patient is placed in the lithotomy position, the genitalia are prepared and draped. Local anesthetic jelly is instilled into urethra U. A 50/50 mixture of 1% plain xylocaine and 0.5% bupivicaine is injected as a periprostatic block. Ten (10) cm$^3$ of this mixture is injected transperineally under digital rectal control lateral to the urethra, from the base of the prostate P on each side, out distally to the prostatic apex.

After preliminary cystoscopy is completed, the above-described instrument (having the size of the sheath equal, e.g., 8.33 mm, i.e. 25 F) is inserted into urethra U to the position of prostatic part P (FIG. 6). (For the sake of simplicity of the drawing, the guide tubes are omitted and only sheath 10 is shown). Then a working element with laser fiber 16 is introduced through auxiliary guide tube 14 with laser fiber 16 being connected to a laser source (not shown). At this point, a bladder neck occlusion balloon 40, the position of which depends on the size of the prostate P and the adequacy of the visualization within the prostatic urethra U, is inserted and inflated to isolate the area between inflated balloon and the distal tip of sheath 10. The condition of the apparatus when the operation is carried out with the use of balloon catheter 42 is shown in FIG. 6.

As a result, balloon B isolates the area between its surface and the tip of sheath 10. The cooling and flushing liquid W is then caused to circulate through the restricted small-volume area between balloon and the instrument's tip without penetrating to bladder B, which may remain empty. As a result, the patient does not experience urge sensation because of overfilling of the urinary bladder. Liquid W is continuously fed through laser-fiber guide tube 14, cooling and flushing the operation area, and flowing out of the system through isolated axial spaces 15a and 15b (FIG. 2). Alternatively, the liquid W may be additionally fed through one of the above-mentioned inner channels, e.g., channel 15a, and removed through another channel, e.g., 15b.

Laser fiber 16 is then fired at four quadrants of the prostate P (4, 8, 2, and 10 o'clock positions) by rotating laser fiber 16 within guide tube 14. This ablates the prostatic tissue in the treated area.

During the operation, liquid W continuously cools the metal part of the laser tip, irrigates the prostatic part P of urethra U and drains from the system through channels 15a and 15b, thus allowing the laser procedure to proceed without emptying the bladder. This permits the operation to be carried out continuously. The continuous cooling of the laser tip significantly extends its service life. Furthermore, when it is necessary to intensify the cooling of operating distal end 16a of laser fiber 16, tube 14, which is moveable, is shifted along sleeve 17 closer to tip 16a, so that the flow of the cooling and washing liquid becomes more concentrated.

When it is necessary to clean laser-emitting opening 20, which may be clogged by the adherent debris of the burned tissue, etc., balloon is deflated and removed from the instrument, while cleaning brush 19, which is connected to the rotary drive motor 35, is inserted axially through auxiliary guide tube 18 to the position of the laser fiber tip. This situation is shown in FIG. 7. FIG. 7 is a view similar to FIG. 6 illustrating the use of the apparatus with balloon temporary removed and the brush temporary inserted.

While the brush rotates from drive motor 35 (FIG. 3), it can be moved axially back and forth until opening 20 are cleaned. After cleaning, which may take only several seconds, brush 19 is then removed, and ultrasonic sound 40 (FIG. 8) is inserted for measuring the degree of ablation of the tissue in area of prostate P.

After the removal of sound 40, balloon catheter B is reinserted, inflated, and the operation is resumed. The pressure developed by the inflow of the liquid expands the prostatic urethra U, thus improving conditions for observation through optical fiber 12.

Operation of the Apparatus without Balloon Catheter

The entire operation can be carried out without the use of a balloon catheter.

After the patient is placed in the lithotomy position, the genitalia are prepared and draped. Local anesthetic jelly is instilled into the urethra U. A 50/50 mixture of 1% plain xylocaine and 0.5% bupivicaine is injected as a periprostatic block. Ten (10) cm$^3$ of this mixture is injected transperineally under digital rectal control lateral to the urethra, from the base of the prostate P on each side, out distally to the prostatic apex.

Figure 9:
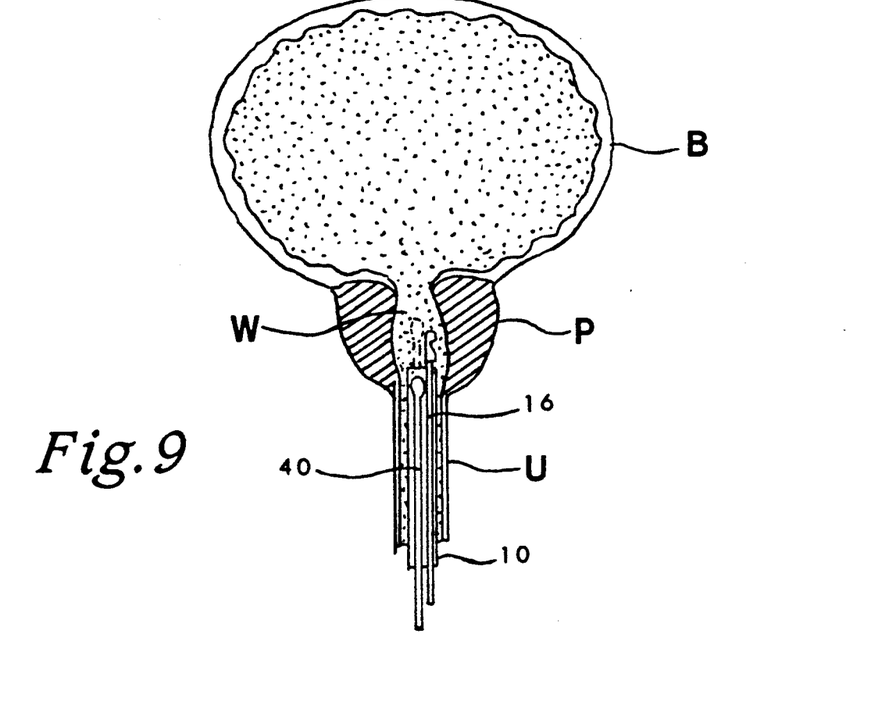
FIG. 9 is a view illustrating the use of the apparatus without the baloon catheter.

FIG. 9 is a view illustrating the use of the apparatus without the baloon catheter.

After preliminary cystoscopy is completed, the above-described instrument (having the size of the sheath equal to 25 F) is inserted into prostatic part of urethra U, and then a working element with laser fiber 16 is introduced through auxiliary guide tube 14 with laser fiber 16 being connected to a laser source (not shown). At this point, bladder B is completely filled with a washing liquid W. Since the prostatic part P of the urethra U is directly connected to the urinary bladder B through the bladder neck, it is also filled with the liquid after filling of the bladder B.

Liquid W is continuously fed through laser-fiber guide tube 14, cooling and flushing the operation area, and flowing out of the system through isolated axial spaces 15a and 15b (FIG. 3). Alternatively, the liquid W may be additionally fed through one of the above-mentioned inner channels, e.g., channel 15a, and removed through another channel, e.g., 15b.

Laser fiber 16 is then fired at four quadrants of the prostate P (4, 8, 2, and 10 o'clock positions) by rotating laser fiber 16 within guide tube 14. This emits the laser through opening 20 and ablates the prostatic tissue in the treated area.

During the operation, liquid W continuously cools the metal part of the laser tip, irrigates the prostatic part P of urethra U and drains from the system through channels 15a and 15b, thus allowing the laser procedure to proceed without emptying this part of the urethra. This permits the operation to be carried out continuously. The continuous cooling of the laser tip significantly extends its service life. Furthermore, when it is necessary to intensify the cooling of operating distal end 16a of laser fiber 16, tube 14, which is moveable, is shifted closer to tip 16a, so that the flow of the cooling and washing liquid becomes more concentrated.

Figure 8:
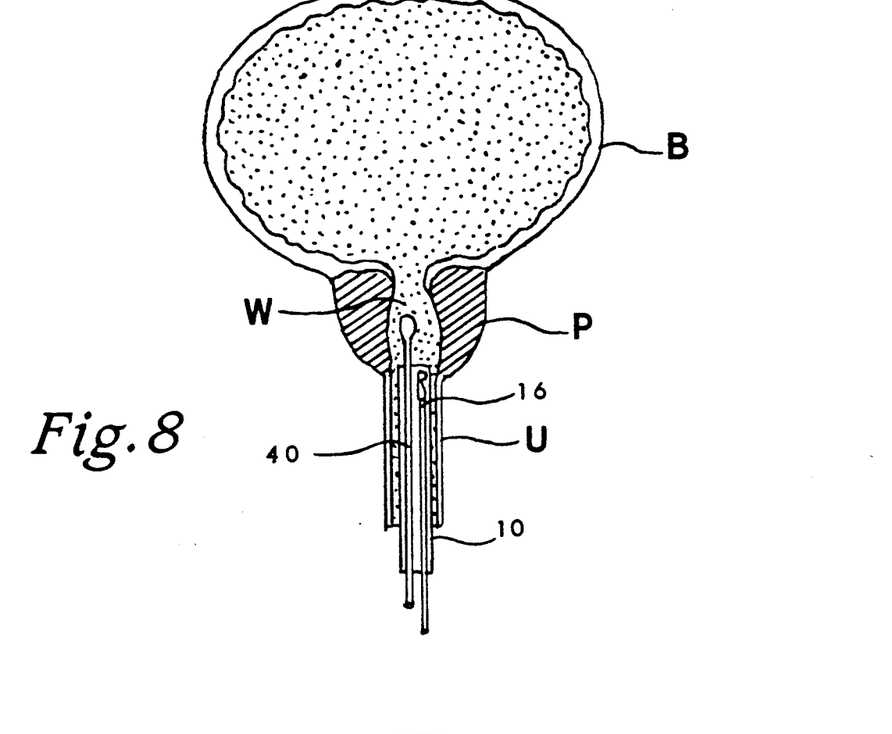
FIG. 8 is a view similar to FIG. 6 illustrating the use of the an ultrasonic sound.

The operation is carried out under periodic control of the depth and degree of ablation of the prostatic tissue by means of ultrasonic sound 40 (FIG. 9), which is constantly present in auxiliary channel 18 (not shown in FIG. 9). When it is necessary to use sound 40, laser fiber 16 is denergized and slightly withdrawn into sheath 10 while sound 40 is pushed forward so that it projects beyond the distal end of tubular outer sheath 10 (similar position of sound 40 and laser fiber 16 is shown in FIG. 8). Under these circumstances, the condition of the tissue can be measured without obstacle. After the measurement is completed, sound 40 is withdrawn into the sheath while laser fiber 16 is moved forward, and the operation procedure is continued.

When it is necessary to clean laser-emitting opening 20, which may be clogged by the adherent debris of the burned tissue, etc., ultrasonic laser 40 is easily removed and is replaced by a cleaning brush 19 (the condition similar to that shown in FIG. 7), which is connected to the rotary drive motor 35. While the brush rotates from drive motor 35, it can be moved axially back and forth until opening 20 is cleaned. After cleaning, which may take only several seconds, brush 19 is then removed, and ultrasonic sound 40 is reinserted for measuring the degree of ablation of the tissue in area of prostate P.

Scope and Ramifications

Thus, it has been shown that the invention provides a method and apparatus for laser-assisted prostatectomy which ensure improved cooling conditions in the operation area, prolong the service life of the apparatus, make it possible to carry out the operation continuously without interruptions to clean the working area, provides an apparatus which is extremely convenient and universal in use, simple in construction, does not obscure the observation of the operation site, and has means for the periodic cleaning of the laser-emitting orifices.

Although the apparatus for laser-assisted prostatectomy been shown and described in the form of one specific embodiment, this embodiment, its parts, materials, and configurations have been given only as examples, and many other modifications of the apparatus are possible. For example, the brush and the laser fiber may be located in a common guide tube having a special cross-sectional configuration for the stabilization of the brush during rotation. The auxiliary guide tube may be used for other instruments, apart from those described in the specification. For example, it can be used for the insertion of a stone disintegration probe. Some parts of the instrument can be made of plastic and be disposable. Although the method has been described with the laser probe fiber the ultrasound probe used alternatingly, the method of laser prostatectomy may be carried out under constant ultrasonic control with the laser fiber and the ultrasonic probe working simultaneously. In other words, any modifications are possible without departure from the scope of the foregoing claims.

What we claim is:

1. A method of laser-assisted prostatectomy comprising the steps of:

providing an apparatus which comprises an elongated tubular sheath which has a distal end and a proximal end and contains a first tube for guiding an axially moveable laser fiber that has at its distal end lateral laser-beam emitting openings, and that can be turned around its longitudinal axis; a second guide tube for guiding a fiber-optic lens system for observation of the operation site; and a third guide tube for guiding one of an auxiliary instrument selected from a group consisting of a balloon catheter, an ultrasonic sound for measuring the depth and degree of ablation of the tissue, and a rotating cleaning brush; each said auxiliary instrument can be inserted into said third guide tube and removed therefrom during the operation of said apparatus; said first, second, and third tubes being arranged parallel to each other in said sheath, the space between the inner surface of said tubular sheath and the outer surface of said guide tubes forming at least two longitudinal channels isolated from each other, one said channel being connected at its proximal end through a shut-off valve to a source of the supply of a flushing and cooling liquid, and another to a reservoir for the removal of said cooling and flushing liquid after its use;

inserting said apparatus into the urethra of a patent suffering from the obstruction of the prostatic part of the urethra to the position in which said distal end of said sheath is in said prostatic part of the urethra;

inserting said balloon catheter through said third guide tube to the position of the inflatable tip of said catheter inside the bladder;

inflating said inflatable tip so as to fix the balloon catheter and to isolate an area between said inflated tip and the operation area within said prostatic urethra from the urinary bladder;

initiating an inflow of said washing and cooling liquid to said prostatic part of the urethra through said first guide tube and outflow of said liquid through said spaces, thus maintaining constant circulation of said liquid through the operation area and said distal end of said laser fiber;

inserting said laser fiber into said first guide tube to the position of said distal end of said laser fiber in said prostatic part; and firing said laser fiber and directing a laser beam laterally from said laser fiber onto said prostatic part of said urethra and rotating said laser fiber during the operation for directing said laser beam to a required area.

2. The method of claim 1, further including the steps of:

deflating said inflatable tip;

removing said balloon catheter from said third guide tube;

inserting into said third guide tube said cleaning brush to the sidewise position with respect to said distal end of said laser fiber;

reciprocating said cleaning brush while causing its rotation thus cleaning said distal end of said laser fiber;

removing said cleaning brush from said third guide tube;

reinserting said balloon catheter and reinflating said inflatable tip; and continuing the operation.

3. The method of claim 1, further including the steps of:

deflating said inflatable tip;

removing said balloon catheter from said third guide tube;

inserting into said third guide tube said cleaning brush to the sidewise position with respect to said distal end of said laser fiber;

reciprocating said cleaning brush while causing its rotation thus cleaning said distal end of said laser fiber;

removing said cleaning brush from said third guide tube;

retracting said laser fiber into said first guide tube;

inserting said ultrasonic sound into said third guide tube to the position of said prostatic part;

measuring the depth and degree of ablation of the tissue;

removing said ultrasonic sound from said third guide tube;

reinserting said balloon catheter and reinflating said inflatable tip; and continuing the operation.

4. A method of laser-assisted prostatectomy comprising the steps of:

providing an apparatus which comprises an elongated tubular sheath which has a distal end and a proximal end and contains a first tube for guiding an axially moveable laser fiber that has at its distal end lateral laser-beam emitting openings, and that can be turned around its longitudinal axis; a second guide tube for guiding a fiber-optic lens system for observation of the operation site; and a third guide tube for guiding one of an auxiliary instrument selected from a group consisting of a balloon catheter, an ultrasonic sound for measuring the depth and degree of ablation of the tissue, and a rotating cleaning brush; each said auxiliary instrument can be inserted into said third guide tube and removed therefrom during the operation of said apparatus; said first, second, and third tubes being arranged parallel to each other in said sheath, the space between the inner surface of said tubular sheath and the outer surface of said guide tubes forming at least two longitudinal channels isolated from each other, one said channel being connected at its proximal end through a shut-off valve to a source of the supply of a flushing and cooling liquid, and another to a reservoir for the removal of said cooling and flushing liquid after its use;

inserting said apparatus into the urethra of a patent suffering from the obstruction of the prostatic part of the urethra to the position in which said distal end of said sheath is in said prostatic part of the urethra;

initiating an inflow of said washing and cooling liquid to said prostatic part of the urethra through said first guide tube and outflow of said liquid through said spaces, thus maintaining constant circulation of said liquid through the operation area and said distal end of said laser fiber;

inserting said laser fiber into said first guide tube to the position of said distal end of said laser fiber in said prostatic part;

firing said laser fiber and directing a laser beam laterally from said laser fiber onto said prostatic part of said urethra and rotating said laser fiber during the operation for directing said laser beam to a required area.

5. The method of claim 4 further including the steps of:

inserting said ultrasonic sound into said third guide tube;

periodically deenergizing said laser fiber, withdrawing said laser fiber into said first guide tube, pushing forward said ultrasonic sound to the area of said prostatic part, measuring the depth and degree of ablation of the tissue, withdrawing said ultrasonic sound into said third guide tube, returning said laser fiber into said position in said prostatic part; and initiating said firing step.

6. The method of claim 4 further including the steps of:

inserting said ultrasonic sound into said third guide tube;

deenergizing said laser fiber;

withdrawing said ultrasonic sound from said third guide tube inserting into said third guide tube said cleaning brush to the sidewise position with respect to said distal end of said laser fiber;

reciprocating said cleaning brush while causing its rotation thus cleaning said distal end of said laser fiber;

removing said cleaning brush from said third guide tube;

inserting said ultrasonic sound into said third guide tube to the position of said prostatic part; and resuming said firing.

7. An apparatus for continuous laser-assisted prostatectomy comprising:

an elongated hollow tubular sheath having an outer surface and an inner surface, said tubular sheath having has a distal end and a proximal end;

a first tube which has an outer surface and an inner surface and is arranged axially movably in said hollow tubular sheath for guiding an insertable and axially moveable laser fiber, said laser fiber having a distal end and lateral laser-beam emitting openings at said distal end;

a second guide tube which has an outer surface and an inner surface and contains an optical lens system for observation of the operation site in a prostatic part of the urethra;

a third guide tube which has an outer surface and an inner surface and contains for guiding one of an auxiliary instrument, said first guide tube, said second guide tube, and said third guide tube being parallel to each other;

at least two axial mutually isolated spaces formed between said inner surface of said sheath and said outer surfaces of said first guide tube, said second guide tube, and said third guide tube, one said space being connected at its proximal end through a shut-off valve to a source of the supply of a flushing and cooling liquid, and another said space being connected to a reservoir for the removal of said cooling and washing liquid.

8. The apparatus of claim 7 wherein said auxiliary instruments are selected from a group consisting of a balloon catheter, an ultrasonic sound for measuring the depth and degree of ablation of the tissue in the area of said operation site, and a rotating cleaning brush.

9. A method of laser-assisted prostatectomy comprising the steps of:

providing an apparatus which comprises an elongated tubular sheath which has a distal end and a proximal end and contains a first tube for guiding an axially moveable laser fiber that has at its distal end lateral laser-beam emitting openings, and that can be turned around its longitudinal axis; a second guide tube for guiding a fiber-optic lens system for observation of the operation site; and a third guide tube for guiding one of an auxiliary instrument selected from a group consisting of a balloon catheter, an ultrasonic sound for measuring the depth and degree of ablation of the tissue, and a rotating cleaning brush; each said auxiliary instrument can be inserted into said third guide tube and removed therefrom during the operation of said apparatus; said first, second, and third tubes being arranged parallel to each other in said sheath, the space between the inner surface of said tubular sheath and the outer surface of said guide tubes forming at least two longitudinal channels isolated from each other, one said channel being connected at its proximal end through a shut-off valve to a source of the supply of a flushing and cooling liquid, and another to a reservoir for the removal of said cooling and flushing liquid after its use;

inserting said apparatus into the urethra of a patent suffering from the obstruction of the prostatic part of the urethra to the position in which said distal end of said sheath is in said prostatic part of the urethra;

inserting said balloon catheter through said third guide tube to the position of the inflatable tip of said catheter inside the bladder;

inflating said inflatable tip so as to fix the balloon catheter and to isolate an area between said inflated tip and the operation area within said prostatic urethra from the urinary bladder;

initiating an inflow of said washing and cooling liquid to said prostatic part of the urethra through said first guide tube and outflow of said liquid through said spaces, thus maintaining constant circulation of said liquid through the operation area and said distal end of said laser fiber;

inserting said laser fiber into said first guide tube to the position of said distal end of said laser fiber in said prostatic part;

firing said laser fiber and directing a laser beam laterally from said laser fiber onto said prostatic part of said urethra and rotating said laser fiber during the operation for directing said laser beam to a required area.

removing said balloon catheter from said third guide tube;

inserting into said third guide tube said cleaning brush to the sidewise position with respect to said distal end of said laser fiber;

reciprocating said cleaning brush while causing its rotation thus cleaning said distal end of said laser fiber;

removing said cleaning brush from said third guide tube;

reinserting said balloon catheter and reinflating said inflatable tip; and continuing the operation.

10. A method of laser-assisted prostatectomy comprising the steps of:

providing an apparatus which comprises an elongated tubular sheath which has a distal end and a proximal end and contains a first tube for guiding an axially moveable laser fiber that has at its distal end lateral laser-beam emitting openings, and that can be turned around its longitudinal axis; a second guide tube for guiding a fiber-optic lens system for observation of the operation site; and a third guide tube for guiding one of an auxiliary instrument selected from a group consisting of a balloon catheter, an ultrasonic sound for measuring the depth and degree of ablation of the tissue, and a rotating cleaning brush; each said auxiliary instrument can be inserted into said third guide tube and removed therefrom during the operation of said apparatus; said first, second, and third tubes being arranged parallel to each other in said sheath, the space between the inner surface of said tubular sheath and the outer surface of said guide tubes forming at least two longitudinal channels isolated from each other, one said channel being connected at its proximal end through a shut-off valve to a source of the supply of a flushing and cooling liquid, and another to a reservoir for the removal of said cooling and flushing liquid after its use;

inserting said apparatus into the urethra of a patent suffering from the obstruction of the prostatic part of the urethra to the position in which said distal end of said sheath is in said prostatic part of the urethra;

inserting said balloon catheter through said third guide tube to the position of the inflatable tip of said catheter inside the bladder;

inflating said inflatable tip so as to fix the balloon catheter and to isolate an area between said inflated tip and the operation area within said prostatic urethra from the urinary bladder;

initiating an inflow of said washing and cooling liquid to said prostatic part of the urethra through said first guide tube and outflow of said liquid through said spaces, thus maintaining constant circulation of said liquid through the operation area and said distal end of said laser fiber;

inserting said laser fiber into said first guide tube to the position of said distal end of said laser fiber in said prostatic part;

firing said laser fiber and directing a laser beam laterally from said laser fiber onto said prostatic part of said urethra and rotating said laser fiber during the operation for directing said laser beam to a required area;

deflating said inflatable tip;

removing said balloon catheter from said third guide tube;

inserting into said third guide tube said cleaning brush to the sidewise position with respect to said distal end of said laser fiber;

reciprocating said cleaning brush while causing its rotation thus cleaning said distal end of said laser fiber;

removing said cleaning brush from said third guide tube;

retracting said laser fiber into said first guide tube;

inserting said ultrasonic sound into said third guide tube to the position of said prostatic part;

measuring the depth and degree of ablation of the tissue;

removing said ultrasonic sound from said third guide tube;

reinserting said balloon catheter and reinflating said inflatable tip; and continuing the operation.

11. A method of laser-assisted prostatectomy comprising the steps of:

providing an apparatus which comprises an elongated tubular sheath which has a distal end and a proximal end and contains a first tube for guiding an axially moveable laser fiber that has at its distal end lateral laser-beam emitting openings, and that can be turned around its longitudinal axis; a second guide tube for guiding a fiber-optic lens system for observation of the operation site; and a third guide tube for guiding one of an auxiliary instrument selected from a group consisting of a balloon catheter, an ultrasonic sound for measuring the depth and degree of ablation of the tissue, and a rotating cleaning brush; each said auxiliary instrument can be inserted into said third guide tube and removed therefrom during the operation of said apparatus; said first, second, and third tubes being arranged parallel to each other in said sheath, the space between the inner surface of said tubular sheath and the outer surface of said guide tubes forming at least two longitudinal channels isolated from each other, one said channel being connected at its proximal end through a shut-off valve to a source of the supply of a flushing and cooling liquid, and another to a reservoir for the removal of said cooling and flushing liquid after its use;

inserting said apparatus into the urethra of a patent suffering from the obstruction of the prostatic part of the urethra to the position in which said distal end of said sheath is in said prostatic part of the urethra;

initiating an inflow of said washing and cooling liquid to said prostatic part of the urethra through said first guide tube and outflow of said liquid through said spaces, thus maintaining constant circulation of said liquid through the operation area and said distal end of said laser fiber;

inserting said laser fiber into said first guide tube to the position of said distal end of said laser fiber in said prostatic part;

inserting said ultrasonic sound into said third guide tube;

firing said laser fiber and directing a laser beam laterally from said laser fiber onto said prostatic part of said urethra and rotating said laser fiber during the operation for directing said laser beam to a required area;

periodically deenergizing said laser fiber, withdrawing said laser fiber into said first guide tube, pushing forward said ultrasonic sound to the area of said prostatic part, measuring the depth and degree of ablation of the tissue, withdrawing said ultrasonic sound into said third guide tube, returning said laser fiber into said position in said prostatic part; and initiating said firing step.

12. An apparatus for continuous laser-assisted prostatectomy comprising:

an elongated hollow tubular sheath having an outer surface and an inner surface, said tubular sheath having a distal end and a proximal end;

a first tube which has an outer surface and an inner surface and is arranged axially movably in said hollow tubular sheath for guiding an insertable and axially moveable laser fiber, said laser fiber having a distal end and lateral laser-beam emitting openings at said distal end;

a second guide tube which has an outer surface and an inner surface and contains an optical lens system for observation of the operation site in a prostatic part of the urethra;

a third guide tube which has an outer surface and an inner surface for guiding one of an auxiliary instrument, said first guide tube, said second guide tube, and said third guide tube being parallel to each other;

at least two axial mutually isolated spaces formed between said inner surface of said sheath and said outer surfaces of said first guide tube, said second guide tube, and said third guide tube, one said space being connected at its proximal end through a first shut-off valve to a source of the supply of a flushing and cooling liquid, and another said space being connected to a reservoir for the removal of said cooling and washing liquid, said auxiliary instruments are selected from a group consisting of a balloon catheter, an ultrasonic sound for measuring the depth and degree of ablation of the tissue in the area of said operation site, and a rotating cleaning brush.

13. The apparatus of claim 12, further including a sleeve which is rigidly attached to said inner surface of said sheath at said distal end of said sheath, said first guide tube being slidingly inserted into said sleeve for guiding axial movements of said first tube.

14. The apparatus of claim 13, further including a second shutoff valve connected to said proximal end of said first guide tube for additional supply of flushing and cooling water through said first guide tube and for cooling said laser fiber.

15. The apparatus of claim 14 wherein said outer surfaces of said first guide tube, of said second guide tube, and of said third guide tube are rigidly and sealingly interconnected into a single unit so that said unit can be removed from said sheath as a whole, said outer surfaces of said first guide tube, said second guide tube, and said third guide tube being in sealing contact with said inner surface of said sheath, so that when said guide tubes are inserted into said sheath, said axial spaces being mutually isolated.

* * * * *